United States Patent [19]
Read

[11] Patent Number: 5,916,816
[45] Date of Patent: *Jun. 29, 1999

[54] STEAM STERILIZATION INDICATOR COMPOSITIONS

[75] Inventor: David M. Read, White Bear Lake, Minn.

[73] Assignee: Minnesota Mining and Manufacturing Company, St, Paul, Minn.

[ * ] Notice: This patent issued on a continued prosecution application filed under 37 CFR 1.53(d), and is subject to the twenty year patent term provisions of 35 U.S.C. 154(a)(2).

[21] Appl. No.: 08/722,835

[22] Filed: Sep. 27, 1996

[51] Int. Cl.$^6$ ...................................................... G01N 21/78
[52] U.S. Cl. ................................ 436/166; 436/1; 422/61; 422/119
[58] Field of Search ................................ 436/1, 164, 166; 422/56–58, 61, 119

[56] References Cited

U.S. PATENT DOCUMENTS

| | | |
|---|---|---|
| 3,360,338 | 12/1967 | Edenbaum . |
| 3,360,339 | 12/1967 | Edenbaum . |
| 3,386,807 | 6/1968 | Edenbaum . |
| 3,471,422 | 10/1969 | Edlein et al. .............................. 260/22 |
| 4,514,361 | 4/1985 | Hirsch ..................................... 422/242 |
| 5,057,433 | 10/1991 | Douglas ..................................... 436/1 |
| 5,064,576 | 11/1991 | Suto ....................................... 252/962 |

FOREIGN PATENT DOCUMENTS

| | | |
|---|---|---|
| 2-211162 | 8/1990 | Japan . |
| 4-364174 | 10/1992 | Japan . |
| 4-62746 | 12/1992 | Japan . |
| 1132334 | 10/1968 | United Kingdom . |
| 1 221 103 | 2/1971 | United Kingdom . |
| 1415782 | 11/1975 | United Kingdom . |
| 1 458 553 | 12/1976 | United Kingdom . |

OTHER PUBLICATIONS

Billmeyer & Saltzman, *Principles of Color Technology*, 2nd Ed., pp. 62–65; 67–92 (1981).

*Primary Examiner*—Lyle A. Alexander
*Attorney, Agent, or Firm*—Jeffrey J. Hohenshell

[57] ABSTRACT

A steam sterilization indicator composition comprising a bismuth compound, a sulfur source, and a compound capable of generating alkaline conditions when exposed to steam; wherein when exposed to steam the composition noticeably changes color and when exposed to dry heat either does not change color or changes color to one that is markedly different from the color formed when the same composition is exposed to steam.

36 Claims, No Drawings

STEAM STERILIZATION INDICATOR COMPOSITIONS

BACKGROUND

The invention relates to indicating ink compositions that change color, preferably to black or dark brown, under sterilization conditions of high temperature and humidity effected during steam sterilization.

In hospitals, clinics and the like, it is standard practice to sterilize various products such as gowns and drapes and various medical devices such as surgical instruments, prior to use by placing them in a steam sterilizer. Where such products or instruments are not pre-packaged in a sterile state it is necessary for the hospital or clinic to sterilize them before use. Furthermore, where these products or instruments are not disposable, and are employed more than once, it is necessary that they be cleaned and otherwise prepared for subsequent use. Prior to such use, however, it is essential that such products or instruments be sterilized. This practice is necessary to avoid infection and prevent contamination from the use of such articles. It is particularly important where the articles have previously been used in the care of other patients. As there is no visual way of determining whether a particular article is sterile or not it has been the practice to use, with the article, when placed in the sterilizer, a color change indicator (e.g., a steam sterilization indicator) that changes color under the steam sterilizing conditions, thus indicating that the particular article or package has been processed through the steam sterilizing cycle.

The indicator may be in the form of a strip, card, or tape, for example, to which an indicating ink composition has been applied. It is generally the practice in sterilizing such articles to gather several articles together and bundle them in a porous wrap held together by pressure-sensitive adhesive tape. The bundle is then placed in a sterilizer with a sterilizing indicator either inserted into or applied to the bundle. Where pressure-sensitive adhesive tapes are used for this purpose, it is convenient to have the sterilization indicator on the tape backing. By observation of the color of the sterilization indicator, one can readily determine whether or not the package has been passed through the sterilization cycle. Steam sensitive compositions and steam sterilization indicator compositions that are generally used for such purposes include a polyvalent metal compound, such as lead carbonate, and sulfur. Color development for such compositions usually involves a change to brown or black. In fact, many conventional steam sterilization indicator compositions that change color in steam sterilization contain lead compounds. Materials printed with such compositions containing lead compounds are increasingly unsuitable due to environmental concerns.

Lead compounds are being replaced by other polyvalent metals such as bismuth. For example, U.S. Pat. No. 3,471, 422 (Edbohm et al.) describes a time-temperature responsive color changing indicator composition based on a compound of a polyvalent metal and a sulfur material. The polyvalent metal is lead, copper, cobalt, nickel, bismuth, or cadmium. Also, Japanese Patent Kokai No. 4[1992]-364,174 (Takemura et al.) and Japanese Patent Kokai No. 4[1992]-62,746 (Koybayashi et al.) describe bismuth compounds that can be combined with sulfur or sulfur compounds such as thioureas to produce indicator compositions for steam sterilization. However, such compositions do not reliably turn black, or even dark brown, and/or they take too long to turn black or dark brown under sterilization conditions of high temperature and humidity, or when exposed to dry heat they undergo a color change that is not markedly different from the color formed when the same composition is exposed to steam. Thus, there is a need for steam sterilization indicator compositions that do not contain lead, but are reliable indicators.

SUMMARY OF THE INVENTION

The present invention provides a steam indicator composition comprising a bismuth compound, a sulfur source, and a compound capable of generating alkaline conditions when exposed to steam, wherein when exposed to steam, after about 2 minutes at 134° C., after about 3 minutes at 132° C., or after about 10 minutes at 121° C., the composition noticeably changes color and when exposed to dry heat, at a temperature of about 141° C. for about 30 minutes, either does not change color or changes color to one that is markedly different from the color formed when the same composition is exposed to steam. Preferably, the sulfur source is selected from the group consisting of elemental sulfur and an organic sulfur compound.

Another embodiment of the present invention is a steam sterilization indicator composition comprising a bismuth compound selected from the group consisting of bismuth oxychloride and bismuth subcarbonate; a sulfur source selected from the group consisting of elemental sulfur, 1-(2-methoxyphenyl)-2-thiourea, 1-allyl-2-thiourea, 1-methyl-2-thiourea, 1-ethyl-2-thiourea, 1,3-dimethyl-2-thiourea, 1-phenyl-3-thiosemicarbazide, 1,3-diphenyl-2-thiourea, 1-benzyl-3-methyl-2-thiourea, 1,3-di-o-tolyl-2-thiourea, 1,3-di-p-tolyl-2-thiourea, 4,6-dihydroxy-2-mercaptopyrimidine, and 2-thiohydantoin; and a compound capable of generating alkaline conditions when exposed to steam, which is selected from the group consisting of sodium carbonate, sodium bicarbonate, lithium carbonate, barium hydroxide, calcium hydroxide, sodium acetate, potassium salt of 2,4-dihydroxybenzoic acid, lithium salt of 2,4-dihydroxybenzoic acid, potassium salt of 2,4,6-trihydroxybenzoic acid, and lithium salt of 2,4,6-trihydroxybenzoic acid. Preferably, the bismuth compound differs from the sulfur source.

Yet another object of the invention is a steam sterilization indicator composition preparable by combining components comprising a bismuth compound selected from the group consisting of bismuth oxychloride and bismuth subcarbonate; a sulfur source selected from the group consisting of elemental sulfur, 1-(2-methoxyphenyl)-2-thiourea, 1-allyl-2-thiourea, 1-methyl-2-thiourea, 1-ethyl-2-thiourea, 1,3-dimethyl-2-thiourea, 1-phenyl-3-thiosemicarbazide, 1,3-diphenyl-2-thiourea, 1-benzyl-3-methyl-2-thiourea, 1,3-di-o-tolyl-2-thiourea, 1,3-di-p-tolyl-2-thiourea, 4,6-dihydroxy-2-mercaptopyrimidine, and 2-thiohydantoin; and a compound capable of generating alkaline conditions when exposed to steam, which is selected from the group consisting of sodium carbonate, sodium bicarbonate, lithium carbonate, barium hydroxide and calcium hydroxide or a base generator e.g. sodium acetate, potassium salt of 2,4-dihydroxybenzoic acid, lithium salt of 2,4-dihydroxybenzoic acid, potassium salt of 2,4,6-trihydroxybenzoic acid, and lithium salt of 2,4,6-trihydroxybenzoic acid.

A further object of the present invention is a steam sterilization indicator comprising a substrate coated on at least a portion of one major surface thereof a steam sterilization indicator composition of the present invention.

DETAILED DESCRIPTION

The present invention provides a steam sterilization indicator composition (i.e., indicating ink composition) that includes a bismuth compound, a sulfur source, and a compound that generates alkaline conditions in the presence of steam. Such compositions are particularly advantageous because they provide more reliable noticeable color changes than conventional bismuth-containing steam sterilization indicator compositions. That is, steam sterilization indicator compositions according to the present invention have two responses: (1) when exposed to steam, they display a noticeable color change (preferably, to black or dark brown); and (2) when exposed to dry heat, they either do not change color or they change color to one that is markedly different from the color formed when the same composition is exposed to steam.

Preferably, the compositions according to the present invention become black or dark brown upon exposure to steam. Significantly, preferred compositions according to the present invention change color to black or dark brown after about 2 minutes in steam at 134° C., after about 3 minutes in steam at 132° C., or after about 10 minutes in steam at 121° C. More preferred compositions according to the present invention change color to black or dark brown after about 2 minutes in steam at 134° C., after about 3 minutes in steam at 132° C., and after about 10 minutes in steam at 121° C.

Also, significantly, when exposed to dry (no steam) heat at a temperature of about 141° C. for about 30 minutes, preferred compositions according to the present invention do not change color or change color to one that is markedly different from the color formed when the same composition is exposed to steam. As used herein, "markedly different" means that there is a significant difference in the colors (e.g., cream vs. dark brown or black), as opposed to slight differences (e.g., cream vs. light brown or brown vs. black).

Suitable bismuth compounds for use in indicator compositions (i.e., indicating ink compositions) according to the present invention include bismuth subcarbonate (basic bismuth carbonate) and bismuth oxychloride. Suitable sources of sulfur include elemental sulfur or sulfur-contaning compounds such as 1-(2-methoxyphenyl)-2-thiourea, 1-allyl-2-thiourea, 1-methyl-2-thiourea, 1-ethyl-2-thiourea, 1,3-dimethyl-2-thiourea, 1-phenyl-3-thiosemicarbazide, 1,3-diphenyl-2-thiourea, 1-benzyl-3-methyl-2-thiourea, 1,3-di-o-tolyl-2-thiourea, 1,3-di-p-tolyl-2-thiourea, 4,6-dihydroxy-2-mercaptopyrimidine, and 2-thiohydantoin. It is believed that other bismuth compounds and sources of sulfur can be used in compositions according to the present invention as long as the resultant steam sterilization indicator composition has two responses: (1) when exposed to steam, they display a noticeable color change (preferably, to black or dark brown); and (2) when exposed to dry heat, they either do not change color or they change color to one that is markedly different from the color formed when the same composition is exposed to steam.

Suitable compounds capable of generating alkaline conditions when exposed to steam for use in indicator compositions according to the present invention include bases such as sodium carbonate, sodium bicarbonate, lithium carbonate, barium hydroxide, and calcium hydroxide, as well as base generators such as sodium acetate, salts of (e.g., potassium and lithium salts) of 2,4-dihydroxybenzoic acid and 2,4,6-trihydroxybenzoic acid. It is believed that other compounds capable of generating alkaline conditions when exposed to steam can be used in indicator compositions according to the present invention as long as the resultant steam sterilization indicator composition has two responses: (1) when exposed to steam, they display a noticeable color change (preferably, to black or dark brown); and (2) when exposed to dry heat, they either do not change color or they change color to one that is markedly different from the color formed when the same composition is exposed to steam. As used herein, when it is said that a compound is capable of generating alkaline conditions when exposed to steam, it is meant that when exposed to steam as would occur in a conventional steam sterilizer, the compound produces a composition having a pH of greater than 7.

As stated above, a preferred endpoint color is black or dark brown. For the purposes of the present invention, black or dark brown can be defined by measuring in reflection the $L^*$, $a^*$, and $b^*$ color coordinates. The color coordinates can be obtained by the CIELAB (CIE 1978) color determination methods described in Billmeyer & Saltzman, *Principles of Color Technology*, 2nd Ed., pp.62–65; 67–91 (1981). For purposes of the present invention preferred shades of black or dark brown preferably have: (1) an $L^*$ of less than about 50 and more preferably, of less than about 40; (2) an $a^*$ of less than about 6.0 and more preferably, of less than about 2.0; or a $b^*$ of less than about 17.0 and more preferably, of less than about 5.0. Particularly preferred compositions according to the present invention meet all of these parameters for the color coordinates.

The binder system for indicator compositions according to the present invention may comprise a film-forming carrier which is permeable to steam in order to obtain a satisfactory color change under steam sterilization conditions. Preferably, binder systems provide steam sterilization indicator compositions with film-forming properties, good adhesion to objects, and heat and moisture resistance. Binder systems based on methyl/n-butylmethacrylate copolymers have been found to be particularly effective. Many other binder systems may be used, however. For example, binder systems cured by ultraviolet irradiation or electron beam bombardment such as urethane-acrylates, epoxyacrylates, and polyester acrylates can be used. Other binder systems include nitrocellulose as disclosed in U.S. Pat. No. 5,057,433 (Douglas), and vinyl resins, such as copolymers of polyvinyl chloride and polyvinyl acetate as disclosed in U.S. Pat. No. 3,360,339 (Edenbaum). Other suitable binder systems are disclosed in U.S. Pat. No. 5,064,576 (Suto).

Solvents can be used in steam sterilization indicator compositions to dissolve the binder resin thus producing the printing ink vehicle. Suitable solvents include those used in conventional steam sterilization indicator compositions. Examples include alcohols, esters, aromatic hydrocarbons, and ketones. Particularly, n-propyl acetate, n-propyl alcohol, methanol, 2-ethoxyethanol, butyl acetate, n-butanol, toluene, cyclohexanone, and mixtures thereof, are preferably used. The solvents are evaporated after coating by drying the substrates in a sufficiently hot oven.

The indicator ink compositions may contain other additives, such as, defoamers, flow aids, fillers, pigments, plasticizers, surfactants, and the like. Examples of such additives are disclosed in U.S. Pat. Nos. 3,360,339 (Edenbaum), 3,471,422 (Edbohm et al.), 3,386,807 (Edenbaum), 5,057,433 (Douglas), and 5,064,576 (Suto), as well as, Japanese Patent Kokai No. 4[1992]-364,174 (Takemura et al.) and 4[1992]-62,746 (Koybayashi et al.).

Compositions according to the present invention are prepared by admixing the components of the binder system (binder resin and solvent) and color change chemistry (bismuth compound, source of sulfur, and compound capable of generating alkaline conditions when exposed to steam) in a mixer, ball mill, or attriter, for example. The binder system (binder resin and solvent) is preferably about 50% to about 97% by weight of the indicator ink composition, and the color change chemistry is preferably about 3% to about 50% by weight of the indicator ink composition, based on the total weight of the composition. More preferably, the indicator ink composition includes about 20% to about 35% by weight of the color change chemistry, based on the total weight of the composition.

Preferred indicator ink compositions according to the invention have the following formulations.

|  | General Range in Weight Percent |
| --- | --- |
| bismuth compound | 1–50 |
| sulfur source | 1–20 |
| alkaline-generating compound | 1–20 |
| binder resin | 5–50 |
| solvent | 20–92 |

A particularly preferred indicator ink composition according to the invention has the following formulation.

| bismuth subcarbonate | 19.8 wt-% |
| --- | --- |
| 1,3-diphenyl-2-thiourea | 4.9 wt-% |
| lithium carbonate | 4.5 wt-% |
| methyl/n-butylmethacrylate copolymer | 14.2 wt-% |
| n-propyl acetate | 34.0 wt-% |
| n-propyl alcohol | 22.6 wt-% |

The indicator elements of the invention may comprise any substrate which is capable of withstanding steam sterilization conditions (i.e., temperatures of about 120° C. to about 140° C. for a period of up to about 30 minutes. Suitable substrates include paper which may or may not be saturated with a rubber/resin solution or a natural or synthetic latex, coated paper, cardboard, plastics, metallised material, metal foil and nonwoven or woven textile materials.

In one preferred form, the substrate is in the form of a tape, more preferably a pressure sensitive adhesive tape having a release coating upon one surface and a pressure sensitive adhesive on the other such that the tape may be wound in the form of a roll. A second preferred form comprises a rectangular or square test sheet having an area on which the indicator ink composition has been applied. Other substrates may be in the form of a bag or other wrapping in which case the indicator ink composition may be confined to small areas.

Indicator ink compositions according to the present invention may be printed by a range of printing techniques, such as flexographic, rotogravure and screen printing. The compositions are usually applied in the form of patterns such as stripes, chevrons, etc., in order to provide a visual contrast between areas of the indicator which will provide a visual change after steam sterilization and background areas of the indicator. However, the use of patterns is not essential and the indicator may be completely coated, e.g., by a web coating technique.

The invention will now be illustrated by the following Examples.

Advantages of the invention are illustrated by the following examples. However, the particular materials and amounts thereof recited in these examples, as well as other conditions and details, are to be interpreted to apply broadly in the art and should not be construed to unduly limit the invention.

EXAMPLES

Preparation of Metal Salts of Hydroxybenzoic Acids

The base generators that are metal salts of hydroxybenzoic acids were prepared by treating the parent (2,4-di- or 2,4,6-tri-) hydroxybenzoic acid (1 mole) (commercially available from Aldrich Chemical Company Inc., Milwaukee, Wis.) with the appropriate metal carbonate. The metal (potassium or lithium) carbonate (0.95 mole) (commercially available from Fisher Company, Fair Lawn, N.J.) was dissolved in water. The parent acid was suspended in water and the metal carbonate solution was slowly added to the suspension through a dropping funnel to form a solution of the metal salt. The solution was filtered and the aqueous filtrate was allowed to evaporate at room temperature. The resulting solid was triturated with ether to remove unreacted acid and the solid metal salt of the acid dried at room temperature.

Preparation of Indicating Ink Compositions

Indicating ink compositions were prepared by mixing 25 grams of a binder solution containing 25 weight percent methyl/n-butylmethacrylate copolymer (commercially available as ELVACITE 2013 from E.I. Du Pont de Nemours, Wilmington Del.) in a mixture of 60 n-propyl acetate:40 n-propyl alcohol (v:v ratio) with the components in the amounts given in Tables 1–28. The indicating ink compositions were mixed in glass jars containing glass marbles. The glass jars were rolled overnight on a roller mill.

Coating of Indicating Ink Composition to Make an Indicator

The resulting ink suspension was coated on a treated paper backing (commercially available as "No. C88742" from Kimberly-Clark Corporation, Munising, Mich.) using a number 20 Meyer bar (commercially available from R. D. Specialties, Webster, N.Y.). The coated ink was dried at 66° C. in an oven (commercially available as "DESPATCH Style V 29" from Despatch Oven Co., Minneapolis, Minn.).

Test Methods

The ink coated paper backing was cut into strips 2.5 cm wide and 20 cm long and exposed to a prevacuum steam sterilization cycle in a Joslyn "BIER" Vessel from Joslyn Valve Company, Macedon, N.Y. Each strip was evaluated visually for color change after 30 seconds at 134° C., after 2 minutes at 134° C., after 3 minutes at 121° C., or after 10 minutes at 121° C. For the Joslyn "BIER" Vessel the indicating ink composition should be a darker color after 2 minutes in steam at 134° C. than it is after 30 seconds at 134° C., and it should be a darker color after 10 minutes in steam at 121° C. than it is after 3 minutes at 121° C. The results of this test are reported in Tables 1–28.

AMSCO 3013-C Sterilizer Steam Sterilization Test

The ink coated paper backing was cut into strips 2.5 cm wide and 20 cm long and exposed to steam conditions in an AMSCO 3013-C Sterilizer from American Sterilization Company (AMSCO), Erie, Pa. The test conditions involved a prevacuum cycle at 132° C. or a gravity cycle at 121° C. Each strip was evaluated visually for color after 0 minutes at 132° C. (i.e., initially upon the strips reaching 132° C.), after 3 minutes at 132° C., after 3 minutes at 121° C., or after 10 minutes at 121° C. For the AMSCO 3013-C Sterilizer the indicating ink composition should be a darker color after 3 minutes in steam at 132° C. than it was initially and it should be a darker color after 10 minutes in steam at 121° C. than it is after 3 minutes at 121° C. The symbols '0/1', '3/1', and '10/1' mean the number of minutes in steam followed by the number of minutes dried. The results of this test are reported in Tables 1–28.

Dry Heat Test

The ink coated paper backing was cut into strips 2.5 cm wide and 20 cm long and exposed to dry heat (i.e., no steam) in a laboratory oven (Tenney, Jr.). The strips were evaluated for color change after 30 minutes at 141° C. The results of this test are reported in Tables 1–28 as a pass or fail. "Pass" means there is no color change or there is a color change that is markedly different from the color formed when the same composition is exposed to steam under the conditions described herein in the steam sterilization tests.

EXAMPLE 1

Indicator inks were prepared as described above with the components in the amounts given in Table 1. The ink suspension was coated, dried and tested as described above. The results of adding a variety of bases or base generators to bismuth subcarbonate and sulfur are shown in Table 1.

The components for Comparison Run 1C and Comparison Run 6C were described in Japanese Patent Kokai No. 4[1992]-364,174. The addition of sodium carbonate to the bismuth subcarbonate and sulfur had a positive effect on the color development as a result of steam sterilization in Run 2 as compared to the color changes without the base in Comparison Run 1C, which had almost no reaction. Comparison Run 3C had a slight color change in the AMSCO sterilizer at the higher temperature. In Comparison Run 4C the base generator, sodium acetate, had no significant effect on the color change compared to Comparison Run 1C. The addition of a potassium salt of 2,4-dihydroxybenzoic acid to the bismuth subcarbonate and sulfur had a positive effect on the color development as a result of steam sterilization in Run 5 as compared to the color changes without the base in Comparison Run 1C.

EXAMPLE 2

Indicator inks were prepared as described above with the components in the amounts given in Table 2. The ink suspension was coated, dried and tested as described above. The results of adding a variety of bases or base generators to bismuth subcarbonate and 1-(2-methoxyphenyl)-2-thiourea are shown in Table 2.

Comparison Run 1C, which had no base or base generator, had almost no reaction to steam in the Joslyn BIER Vessel. Comparison Run 2C, which had sodium carbonate added failed the dry heat test, but in the Joslyn BIER Vessel turned black after 2 minutes. Runs 3 and 4 contained a base generator and varying amounts of the bismuth compound. The base generator allowed these compositions to pass the dry heat test and turn black in the sterilization cycles at 132° C.

TABLE 1

| Run No. | Components<br>a) Bismuth compound<br>b) Sulfur compound<br>c) Base or base generator | Response in Joslyn BIER Vessel (color after) | | | | | Dry Heat | Response in AMSCO 3013-C Sterilizer (color after) | | | |
|---|---|---|---|---|---|---|---|---|---|---|---|
| | | 30 sec 134° C. | 2 min 134° C. | 3 min 121° C. | 10 min 121° C. | 30 min 141° C. | | 0/1 min 132° C. | 3/1 min 132° C. | 3/1 min 121° C. | 10/1 min 121° C. |
| 1C | Bismuth subcarbonate[2] 5 g<br>Sulfur[3] 3.5 g | Cream | Pale Yellow | Cream | Pale Yellow | Fail Pale Yellow | | Pale Yellow | Yellow[1] | | |
| 2 | Bismuth subcarbonate[2] 5 g<br>Sulfur[3] 3.5 g<br>Sodium carbonate[4] 0.5 g | Yellow | Brown | Light Mottled Brown | Black | Pass | | Yellow | Black | Dark Yellow Brown | Black |
| 3C | Bismuth subcarbonate[2] 5 g<br>Sulfur[3] 5 g<br>Lithium carbonate[5] 1.5 g | | | | | | | | Beige | | |
| 4C | Bismuth subcarbonate[2] 7 g<br>Sulfur[3] 3.5 g<br>Sodium acetate[6] 0.5 g | White | Buff | Yellow | Buff | Fail Buff | | | | | |
| 5 | Bismuth subcarbonate[2] 5 g<br>Sulfur[3] 3.5 g<br>2,4-dihydroxybenzoic acid K[8] 1 g | Light Brown | Black | Medium Brown | Dark Brown | Pass White | | Black | Black | Very Dark Brown | Very Dark Brown |
| 6C | Bismuth subcarbonate[2] 7 g<br>Sulfur[3] 7 g | | | | | | | Light Yellow | Very Light Brown | | |

[1]Darker after 5 minutes.
[2]Commercially available from J. T. Baker, Inc., Phillipsburg, NJ.
[3]Commercially available from Akrochem Corporation, Akron, OH.
[4]Commercially available from Aldrich Chemical Company, Inc., Milwaukee, WI.
[5]Commercially available from Fisher Chemical Company, Fair Lawn, NJ.
[6]Commercially available from Mallinckrodt Chemical Company, St. Louis MO.
[8]Prepared as described above.

TABLE 2

| | Components<br>a) Bismuth compound | | Response in<br>Joslyn BIER Vessel<br>(color after) | | | | Dry<br>Heat | Response in<br>AMSCO 3013-C Sterilizer<br>(color after) | | | |
|---|---|---|---|---|---|---|---|---|---|---|---|
| Run<br>No. | b) Sulfur compound<br>c) Base or base generator | 30 sec<br>134° C. | 2 min<br>134° C. | 3 min<br>121° C. | 10 min<br>121° C. | 30 min<br>141° C. | | 0/1 min<br>132° C. | 3/1 min<br>132° C. | 3/1 min<br>121° C. | 10/1 min<br>121° C. |
| 1C | Bismuth subcarbonate[2] 7 g<br>1-(2-Methoxyphenyl)-2-thiourea[4] 1.75 g | Buff | Light<br>Brown | Very<br>Light<br>Brown | Light<br>Brown | | | | | | |
| 2C | Bismuth subcarbonate[2] 7 g<br>1-(2-Methoxyphenyl)-2-thiourea[4] 1.75 g<br>Sodium carbonate[4] 0.5 g | Very<br>Dark<br>Brown | Black | | | Fail | | | | | |
| 3 | Bismuth subcarbonate[2] 10 g<br>1-(2-Methoxyphenyl)-2-thiourea[4] 1.75 g<br>2,4-Dihydroxybenzoic acid K[8] 2 g | Buff | Dark<br>Brown | Buff | Brown | Pass<br>White | | Black | Black | Buff | Brown |
| 4 | Bismuth subcarbonate[2] 7 g<br>1-(2-Methoxyphenyl)-2-thiourea[4] 1.75 g<br>2,4-Dihydroxybenzoic acid K[8] 2 g | Buff | Brown | Buff | Brown | Pass | | Black | Black | Buff | Dark<br>Brown |

[2]Commercially available from J. T. Baker, Inc., Phillipsburg, NJ.
[4]Commercially available from Aldrich Chemical Company, Inc., Milwaukee, WI.
[8]Prepared as described above.

EXAMPLE 3

Indicator inks were prepared as described above with the components in the amounts given in Table 3. The ink suspension was coated, dried and tested as described above. The results of adding sodium carbonate to bismuth subcarbonate and 1-allyl-2-thiourea are shown in Table 3.

The indicator ink composition in Comparison Run 1C did not turn black in either sterilizer and failed the dry heat test. When a base was added to the composition in Run 2, it passed the dry heat test and rapidly turned black in both sterilizers.

pension was coated, dried and tested as described above. The results of adding sodium carbonate to bismuth subcarbonate and 1-methyl-2-thiourea and of using bismuth subnitrate instead of bismuth subcarbonate are shown in Table 4.

Comparison Run 1C is a composition described in Japanese Patent Kokai No. 4[1992]-62,746. This composition did not turn black. When a base was added to the composition in Run 2, it rapidly turned black in both sterilizers. Comparison Run 3C, which used bismuth subnitrate, failed the dry heat test.

TABLE 3

| | Components<br>a) Bismuth compound | | Response in<br>Joslyn BIER Vessel<br>(color after) | | | | Dry<br>Heat | Response in<br>AMSCO 3013-C Sterilizer<br>(color after) | | | |
|---|---|---|---|---|---|---|---|---|---|---|---|
| Run<br>No. | b) Sulfur compound<br>c) Base or base generator | 30 sec<br>134° C. | 2 min<br>134° C. | 3 min<br>121° C. | 10 min<br>121° C. | 30 min<br>141° C. | | 0/1 min<br>132° C. | 3/1 min<br>132° C. | 3/1 min<br>121° C. | 10/1 min<br>121° C. |
| 1C | Bismuth subcarbonate[2] 7 g<br>1-Allyl-2-thiourea[4] 1.75 g | Very Dark<br>Beige | Brown | Dark<br>Beige | Brown | Fail<br>Dark<br>Yellow/<br>Brown | | Light<br>Brown | Brown[1] | | |
| 2 | Bismuth subcarbonate[2] 7 g<br>1-Allyl-2-thiourea[4] 1.75 g<br>Sodium carbonate[4] 0.5 g | Dark<br>brown | Black | Black | Black | Pass<br>Dark<br>Yellow | | Dark<br>Brown | Black | | |

[1]Same after 5 minutes
[2]Commercially available from J. T. Baker, Inc., Phillipsburg, NJ.
[4]Commercially available from Aldrich Chemical Company, Inc., Milwaukee, WI.

EXAMPLE 4

Indicator inks were prepared as described above with the components in the amounts given in Table 4. The inksus-

TABLE 4

| | Components<br>a) Bismuth compound | Response in Joslyn BIER Vessel (color after) | | | | Dry Heat | Response in AMSCO 3013-C Sterilizer (color after) | | | |
|---|---|---|---|---|---|---|---|---|---|---|
| Run No. | b) Sulfur compound<br>c) Base or base generator | 30 sec 134° C. | 2 min 134° C. | 3 min 121° C. | 10 min 121° C. | 30 min 141° C. | 0/1 min 132° C. | 3/1 min 132° C. | 3/1 min 121° C. | 10/1 min 121° C. |
| 1C | Bismuth subcarbonate[2] 7 g<br>1-Methyl-2-thiourea[4] 1.75 g | Beige | Brown | Beige | Light Brown | Pass Cream with Black Spots | Dark beige | Brown | | |
| 2 | Bismuth subcarbonate[2] 7 g<br>1-Methyl-2-thiourea[4] 1.75 g<br>Sodium carbonate[4] 0.5 g | Black | Black | | | Pass Beige with Black Spots | Black | Black | Black | Black |
| 3C | Bismuth subnitrate[4] 7 g<br>1-Methyl-2-thiourea[4] 1.75 g | Medium Brown | Dark Brown | Very Dark Yellow | Black | Fail Black | Black | Black | | |

[2]Commercially available from J. T. Baker, Inc., Phillipsburg, NJ.
[4]Commercially available from Aldrich Chemical Company, Inc., Milwaukee, WI.

EXAMPLE 5

Indicator inks were prepared as described above with the components in the amounts given in Table 5. The ink suspension was coated, dried and tested as described above. The results of adding sodium carbonate to bismuth subcarbonate and 1-ethyl-2-thiourea and of using bismuth subnitrate instead of bismuth subcarbonate are shown in Table 5.

Comparison Run 1C is another composition described in Japanese Patent Kokai No. 4[19923]-62,746. The composition did not turn black. By adding base to the composition in Run 2, the color of the ink composition changed to black in steam sterilization conditions. Bismuth subnitrate was used in Comparison Run 3C and that composition failed the dry heat test.

EXAMPLE 6

Indicator inks were prepared as described above with the components in the amounts given in Table 6. The ink suspension was coated, dried and tested as described above. The results of adding various bases to bismuth subcarbonate and 1,3-dimethyl-2-thiourea and of changing ratios of bismuth compound to sulfur compound are shown in Table 6.

Comparison Run 1C, which had no base or base generator, had almost no reaction to steam in the AMSCO sterilizer. When a base was added to the composition in Run 2, it rapidly turned black in both sterilizers. Run 3 had a lower sulfur compound concentration than Run 2, but the results were similar. Magnesium carbonate was used as a base in Comparison Run 4C, but the indicator ink composition did not turn black in either steam sterilizer.

TABLE 5

| | Components<br>a) Bismuth compound | Response in Joslyn BIER Vessel (color after) | | | | Dry Heat | Response in AMSCO 3013-C Sterilizer (color after) | | | |
|---|---|---|---|---|---|---|---|---|---|---|
| Run No. | b) Sulfur compound<br>c) Base or base generator | 30 sec 134° C. | 2 min 134° C. | 3 min 121° C. | 10 min 121° C. | 30 min 141° C. | 0/1 min 132° C. | 3/1 min 132° C. | 3/1 min 121° C. | 10/1 min 121° C. |
| 1C | Bismuth subcarbonate[2] 7 g<br>1-Ethyl-2-thiourea[4] 1.75 g | Beige | Light Brown | Dark Cream | Darker Cream | Light Brown | Brown[1] | | | |
| 2 | Bismuth subcarbonate[2] 7 g<br>1-Ethyl-2-thiourea[4] 1.75 g<br>Sodium carbonate[4] 2 g | Black | Black | Black | Black | Pass Dark Yellow | | | | |
| 3C | Bismuth subnitrate[4] 7 g<br>1-Ethyl-2-thiourea[4] 1.75 g | Black | Black | Medium Brown | Black | Fail Black | | | | |

[1]Same after 6 minutes.
[2]Commercially available from J. T. Baker, Inc., Phillipsburg, NJ.
[4]Commercially available from Aldrich Chemical Company, Inc., Milwaukee, WI.

TABLE 6

| Run No. | Components<br>a) Bismuth compound<br>b) Sulfur compound<br>c) Base or base generator | Response in Joslyn BIER Vessel (color after) | | | | Dry Heat | Response in AMSCO 3013-C Sterilizer (color after) | | | |
|---|---|---|---|---|---|---|---|---|---|---|
| | | 30 sec 134° C. | 2 min 134° C. | 3 min 121° C. | 10 min 121° C. | 30 min 141° C. | 0/1 min 132° C. | 3/1 min 132° C. | 3/1 min 121° C. | 10/1 min 121° C. |
| 1C | Bismuth subcarbonate[2] 7 g<br>1,3-Dimethyl-2-thiourea[4] 7 g | | | | | Gray | Light Gray | | Gray | |
| 2 | Bismuth subcarbonate 7 g 1,3-Dimethyl-2-thiourea[4] 7 g<br>Sodium carbonate[4] 0.5 g | Mottled Black | Black | | | Pass | Mottled Black | | Black | |
| 3 | Bismuth subcarbonate[2] 7 g 1,3-Dimethyl-2-thiourea[4] 3.5 g<br>Sodium carbonate[4] 0.5 g | White | Black | Dark Gray | Dark Gray | Pass | Dark Mottled Brown | | Black | |
| 4C | Bismuth subcarbonate[2] 7 g<br>1,3-Dimethyl-2-thiourea[4] 7 g<br>Magnesium carbonate[7] 1 g | Very Light Cream | | | | | Very Light Cream | | | |

[2]Commercially available from J. T. Baker, Inc., Phillipsburg, NJ.
[4]Commercially available from Aldrich Chemical Company, Inc., Milwaukee, WI.
[7]Commercially available from Matheson, Coleman and Bell, Norwood, OH.

EXAMPLE 7

Indicator inks were prepared as described above with the components in the amounts given in Table 7. The ink suspension was coated, dried and tested as described above. The results of adding various bases to bismuth subcarbonate and 1,3-diisopropyl-2-thiourea are shown in Table 7.

Comparison Run 1C had no reaction to steam in the Joslyn BIER Vessel. Comparison Run 2C showed that the addition of a base had little effect and in Comparison Run 3C, which used a stronger base, the result was the same. In this composition the sulfur compound, a di-substituted thiourea, apparently did not desulfurize to form bismuth sulfide.

EXAMPLE 8

Indicator inks were prepared as described above with the components in the amounts given in Table 8. The ink suspension was coated, dried and tested as described above. The results of adding various bases to bismuth subcarbonate and 1,3-dibutyl-2-thiourea are shown in Table 8.

Comparison Run 1C had no reaction to steam in the Joslyn BIER™ Vessel. Comparison Run 2C, Comparison Run 3C, and Comparison Run 4C show the results of adding different (Comparison Run 3C) and stronger (Comparison Run 4C) bases. Again the thiourea was di substituted and apparently did not desulfurize to form bismuth sulfide, hence the base had little effect on the results.

TABLE 7

| Run No. | Components<br>a) Bismuth compound<br>b) Sulfur compound<br>c) Base or base generator | Response in Joslyn BIER Vessel (color after) | | | | Dry Heat | Response in AMSCO 3013-C Sterilizer (color after) | | | |
|---|---|---|---|---|---|---|---|---|---|---|
| | | 30 sec 134° C. | 2 min 134° C. | 3 min 121° C. | 10 min 121° C. | 30 min 141° C. | 0/1 min 132° C. | 3/1 min 132° C. | 3/1 min 121° C. | 10/1 min 121° C. |
| 1C | Bismuth subcarbonate[2] 7 g<br>1,3-Dipropyl-2-thiourea[4] 1.75 g | Cream | Cream | | | Yellow | | | | |
| 2C | Bismuth subcarbonate[2] 7 g<br>1,3-Dipropyl-2-thiourea[4] 1.75 g<br>Sodium carbonate[4] 0.5 g | White | Mottled Light Gray | | | Pass | | | | |
| 3C | Bismuth subcarbonate[2] 7 g<br>1,3-Dipropyl-2-thiourea[4] 1.75 g<br>Potassium hydroxide[2] 0.5 g | | Cream | | | | | Light Brown | | |

[2]Commercially available from J. T. Baker, Inc., Phillipsburg, NJ.
[4]Commercially available from Aldrich Chemical Company, Inc., Milwaukee, WI.

TABLE 8

| Run No. | Components<br>a) Bismuth compound<br>b) Sulfur compound<br>c) Base or base generator | Response in Joslyn BIER Vessel (color after) | | | | | Dry Heat | Response in AMSCO 3013-C Sterilizer (color after) | | | |
|---|---|---|---|---|---|---|---|---|---|---|---|
| | | 30 sec 134° C. | 2 min 134° C. | 3 min 121° C. | 10 min 121° C. | 30 min 141° C. | | 0/1 min 132° C. | 3/1 min 132° C. | 3/1 min 121° C. | 10/1 min 121° C. |
| 1C | Bismuth subcarbonate[2] 7 g<br>1,3-Dibutyl-2-thiourea[4] 1.75 g | Cream | Buff | Cream | Buff | Buff | | | | | |
| 2C | Bismuth subcarbonate[2] 7 g<br>1,3-Dibutyl-2-thiourea[4] 1.75 g<br>Sodium carbonate[4] 0.5 g | Cream | Light Gray | | | | Pass | | | | |
| 3C | Bismuth subcarbonate[2] 7 g<br>1,3-Dibutyl-2-thiourea[4] 1.75 g<br>Lithium carbonate[5] 0.5 g | Cream | Dark Yellow | Yellow | Very Dark Yellow | Pass | | | | | |
| 4C | Bismuth subcarbonate[2] 7 g<br>1,3-Dibutyl-2-thiourea[4] 1.75 g<br>Potassium hydroxide[2] 0.5 g | | Beige | | | | | | | Light Brown | |

[2]Commercially available from J. T. Baker, Inc., Phillipsburg, NJ.
[4]Commercially available from Aldrich Chemical Company, Inc., Milwaukee, WI.
[5]Commercially available from Fisher Chemical Company, Fair Lawn, NJ.

EXAMPLE 9

Indicator inks were prepared as described above with the components in the amounts given in Table 9. The ink suspension was coated, dried and tested as described above. The results of adding various bases and base generators to bismuth subcarbonate and 1,3-diphenyl-2-thiourea are shown in Table 9.

Comparison Run 1C is another composition described in Japanese Patent Kokai No. 4[1992]-62,746 and in U.S. Pat. No. 3,471,422. However, it had almost no reaction to steam in the Joslyn BIER Vessel. The indicating ink composition turned black very quickly in Run 2, Run 3, Run 4, Run 7, Run 8, Run 10, Run 11, Run 12, Run 13, Run 14 and Run 15 as a result of adding different bases. Adding calcium carbonate (Comparison Run 5C), zinc oxide (Comparison Run 6C), and magnesium carbonate (Comparison Run 9C) had little effect on the color change of the ink compositions in dry heat or steam sterilization conditions. Run 7 showed that doubling the concentration of this thiourea increased the speed of the color change in sterilization conditions. Run 12 specifically showed that doubling the concentration of base generator increased the rate of the color change. The composition in Run 13 gave particularly fast reaction. Run 14 showed that decreasing the concentration of the thiourea used in Run 8 decreased the rate of the color change. Run 15 illustrated a dry heat response where the color changed in dry heat, but it was markedly different from the color change in steam sterilization conditions.

TABLE 9

| Run No. | Components<br>a) Bismuth compound<br>b) Sulfur compound<br>c) Base or base generator | Response in Joslyn BIER Vessel (color after) | | | | | Dry Heat | Response in AMSCO 3013-C Sterilizer (color after) | | | |
|---|---|---|---|---|---|---|---|---|---|---|---|
| | | 30 sec 134° C. | 2 min 134° C. | 3 min 121° C. | 10 min 121° C. | 30 min 141° C. | | 0/1 min 132° C. | 3/1 min 132° C. | 3/1 min 121° C. | 10/1 min 121° C. |
| 1C | Bismuth subcarbonate[2] 7 g<br>1,3-Diphenyl-2-thiourea[4] 1.75 g | Cream | Buff | | | | Buff | | | | |
| 2 | Bismuth subcarbonate[2] 7 g<br>1,3-Diphenyl-2-thiourea[4] 1.75 g<br>Sodium carbonate[4] 0.5 g | Very Dark Brown | Black | | | | Pass | | | | |
| 3 | Bismuth subcarbonate[2] 7 g<br>1,3-Diphenyl-2-thiourea[4] 1.75 g<br>Lithium carbonate[5] 1.6 g | Beige | Dark Brown | Brown | Black | | Pass Cream | | | | Black |
| 4 | Bismuth subcarbonate[2] 7 g<br>1,3-Diphenyl-2-thiourea[4] 1.75 g<br>Calcium hydroxide[5] 0.88 g | Brown | Very Dark Brown | Dark Brown | Black | | Pass | Medium Brown | Very Dark Brown | | |
| 5C | Bismuth subcarbonate[2] 7 g<br>1,3-Diphenyl-2-thiourea[4] 1.75 g<br>Calcium carbonate[6] 1.75 g | Cream | Beige | | | | Pass | Beige | Beige | | |
| 6C | Bismuth subcarbonate[2] 7 g<br>1,3-Diphenyl-2-thiourea[4] 1.75 g<br>Zinc Oxide[6] 1.75 g | Light Cream | Light Cream | | | | | Beige | Beige | | |
| 7 | Bismuth subcarbonate[2] 7 g<br>1,3-Diphenyl-2-thiourea[4] 3.5 g<br>Sodium carbonate[4] 0.5 g | Black | Black | | | | Pass | Black | Black | | |
| 8 | Bismuth subcarbonate[2] 7 g<br>1,3-Diphenyl-2-thiourea[4] 1.75 g<br>Sodium bicarbonate[7] 0.5 g | Very Dark Brown | Black | | | | Pass | | | | |
| 9 | Bismuth subcarbonate[2] 7 g<br>1,3-Diphenyl-2-thiourea[4] 0.5 g | Dark Cream | Light Brown | Buff | Light Brown | | Fail Light | | | | |

TABLE 9-continued

| Run No. | Components<br>a) Bismuth compound<br>b) Sulfur compound<br>c) Base or base generator | Response in Joslyn BIER Vessel (color after) | | | | Dry Heat | Response in AMSCO 3013-C Sterilizer (color after) | | | |
|---|---|---|---|---|---|---|---|---|---|---|
| | | 30 sec 134° C. | 2 min 134° C. | 3 min 121° C. | 10 min 121° C. | 30 min 141° C. | 0/1 min 132° C. | 3/1 min 132° C. | 3/1 min 121° C. | 10/1 min 121° C. |
| 10 | Magnesium carbonate[7] 0.5 g<br>Bismuth subcarbonate[2] 7 g<br>1,3-Diphenyl-2-thiourea[4] 1.75 g<br>Sodium acetate[6] 0.5 g | Brown | Brown | Brown | Brown | Brown Pass | Very Dark Brown | Black | Brown | Dark Brown |
| 11 | Bismuth subcarbonate[2] 7 g<br>1,3-Diphenyl-2-thiourea[4] 1.75 g<br>2,4-Dihydroxybenzoic acid K[8] 1 g | Buff | Dark Brown | Light Brown | Dark Brown | Pass | Very Dark Brown | Black | Buff | Black |
| 12 | Bismuth subcarbonate[2] 7 g<br>1,3-Diphenyl-2-thiourea[4] 1.75 g<br>2,4-Dihydroxybenzoic acid K[8] 2 g | Brown | Black | Dark Brown | Black | Pass | Black | Black | Dark Brown | Black |
| 13 | Bismuth subcarbonate[2] 7 g<br>1,3-Diphenyl-2-thiourea[4] 1.75 g<br>2,4,6-Trihydroxybenzoic acid Li[8] 0.5 g | Very Dark Brown | Black | Black | Black | Pass | Black | Black | Black | Black |
| 14 | Bismuth subcarbonate[2] 7 g<br>1,3-Diphenyl-2-thiourea[4] 0.5 g<br>Sodium bicarbonate[7] 0.5 g | Light Brown | Dull Black | Mottled Dark Brown | Mottled Dark Brown | Pass | Very Dark Gray | Very Dark Brown | Mottled Dark Gray | Black |
| 15 | Bismuth subcarbonate[2] 7 g<br>1,3-Diphenyl-2-thiourea[4] 1.75 g<br>Barium hydroxide[2] 1.6 g | Brown | Dark Brown | Dark Brown | Dark Brown | Pass Yellow Brown[1] | Dark Brown | Black | Dark Brown | Very Dark Brown |

[1]Starting color is beige.
[2]Commercially available from J. T. Baker, Inc., Phillipsburg, NJ.
[4]Commercially available from Aldrich Chemical Company, Inc., Milwaukee, WI.
[5]Commercially available from Fisher Chemical Company, Fair Lawn, NJ.
[6]Commercially available from Mallinckrodt Chemical Company, St. Louis MO.
[7]Commerically available from Matheson, Coleman and Bell, Norwood, OH.
[8]Prepared as described above.

EXAMPLE 10

Indicator inks were prepared as described above with the components in the amounts given in Table 10. The ink suspension was coated, dried and tested as described above. The results of adding various bases to bismuth oxychloride and 1,3-diphenyl-2-thiourea and using thiourea as a sulfur compound are shown in Table 10.

Comparison Run 1C had almost no color change in steam. Run 2 showed that the addition of base caused the indicating ink composition to turn brown. However, by using a different base as in Run 3 the indicating ink composition turned black very rapidly. When thiourea (Comparison Run 4C) was used as the sulfur compound, the ink composition failed the dry heat test.

EXAMPLE 11

Indicator inks were prepared as described above with the components in the amounts given in Table I1. The ink suspension was coated, dried and tested as described above. The results of adding sodium carbonate to bismuth subgallate and 1,3-diphenyl-2-thiourea are shown in Table 11.

Comparison Run 1 became bright yellow in steam and the addition of a base (Comparison Run 2) darkened that color, but the color change was not to black.

TABLE 10

| Run No. | Components<br>a) Bismuth compound<br>b) Sulfur compound<br>c) Base or base generator | Response in Joslyn BIER Vessel (color after) | | | | Dry Heat | Response in AMSCO 3013-C Sterilizer (color after) | | | |
|---|---|---|---|---|---|---|---|---|---|---|
| | | 30 sec 134° C. | 2 min 134° C. | 3 min 121° C. | 10 min 121° C. | 30 min 141° C. | 0/1 min 132° C. | 3/1 min 132° C. | 3/1 min 121° C. | 10/1 min 121° C. |
| 1C | Bismuth oxychloride[4] 7.5 g<br>1,3-Diphenyl-2-thiourea[4] 3.75 g | | Cream | | | | | Dark Cream | | |
| 2 | Bismuth oxychloride[4] 7.5 g<br>1,3-Diphenyl-2-thiourea[4] 3.75 g<br>Sodium bicarbonate[7] 0.25 g | Light Brown | Light Brown | Light Brown | Brown | Pass | Brown | Brown | Brown | Brown |
| 3 | Bismuth oxychloride[4] 7.5 g<br>1,3-Diphenyl-2-thiourea[4] 3.75 g<br>Sodium carbonate[4] 0.5 g | Black | Black | | | Pass | Black | Black | | |
| 4C | Bismuth oxychloride[4] 7.5 g<br>Thiourea[4] 7.5 g | | | | | Black | Black | Black | | |

[4]Commercially available from Aldrich Chemical Company, Inc., Milwaukee, WI.
[7]Commercially available from Matheson, Coleman and Bell, Norwood, OH.

TABLE 11

| Run No. | Components<br>a) Bismuth compound<br>b) Sulfur compound<br>c) Base or base generator | Response in Joslyn BIER Vessel (color after) | | | | Dry Heat | Response in AMSCO 3013-C Sterilizer (color after) | | | |
|---|---|---|---|---|---|---|---|---|---|---|
| | | 30 sec 134° C. | 2 min 134° C. | 3 min 121° C. | 10 min 121° C. | 30 min 141° C. | 0/1 min 132° C. | 3/1 min 132° C. | 3/1 min 121° C. | 10/1 min 121° C. |
| 1C | Bismuth subgallate[2] 7 g<br>1,3-Diphenyl-2-thiourea[4] 1.75 g | | Bright Yellow | | | | | | | |
| 2C | Bismuth subgallate[2] 7 g<br>1,3-Diphenyl-2-thiourea[4] 1.75 g<br>Sodium carbonate[4] 0.5 g | Dark Yellow | Dark Yellow | Dark Yellow | Dark Yellow | | | | | |

[2]Commerically available from J. T. Baker, Inc., Phillipsburg, NJ.
[4]Commercially available from Aldrich Chemical Company, Inc., Milwaukee, WI.

EXAMPLE 12

Indicator inks were prepared as described above with the components in the amounts given in Table 12. The ink suspension was coated, dried and tested as described above. The results of adding sodium carbonate to bismuth (3) oxide and 1,3-diphenyl-2-thiourea in varying ratios are shown in Table 12.

Comparison Run 1C and Comparison Run 3C are similar to a composition described in Japanese Patent Kokai No. 4[19921]-364,174 (Takemura et al.). However, the compositions did not get darker after exposure to steam for the second time interval in either sterilizer. Adding a base to the indicating ink composition of Comparison Run 2 and Comparison Run 4 had little effect on the color change.

suspension was coated, dried and tested as described above. The results of adding sodium carbonate to bismuth subnitrate or bismuth subcarbonate and 1,3-di-o-tolyl-2-hiourea or 1,3-di-ρ-tolyl-2-thiourea are shown in Table 13.

Comparison Run 1C, Comparison Run 3C, Comparison Run 5C, and Comparison Run 7C are similar to compositions described in Japanese Patent Kokai No. 4[1992]-364,174 (Takemura et al.). None of the Comparison Run compositions turned black in steam sterilization conditions. Comparison Run 1C and Comparison Run 5C compositions also failed the dry heat test. The addition of sodium carbonate caused the composition to turn black in Run 4, Comparison Run 6C, and Run 8. However Comparison Run 6C failed the dry heat test. The indicating ink composition in Comparison Run 2C became darker with the addition of base, but failed the dry heat test.

TABLE 12

| Run No. | Components<br>a) Bismuth compound<br>b) Sulfur compound<br>c) Base or base generator | Response in Joslyn BIER Vessel (color after) | | | | Dry Heat | Response in AMSCO 3013-C Sterilizer (color after) | | | |
|---|---|---|---|---|---|---|---|---|---|---|
| | | 30 sec 134° C. | 2 min 134° C. | 3 min 121° C. | 10 min 121° C. | 30 min 141° C. | 0/1 min 132° C. | 3/1 min 132° C. | 3/1 min 121° C. | 10/1 min 121° C. |
| 1C | Bismuth(3) oxide[4] 7 g<br>1,3-Diphenyl-2-thiourea[4] 10 g | Gray | Gray | Gray | Gray | Pass Off White | Gray[1] | | | |
| 2C | Bismuth(3) oxide[4] 7 g<br>1,3-Diphenyl-2-thiourea[4] 10 g<br>Sodium carbonate[4] 3 g | Gray | Gray[3] | Gray | Very Light Brown | Pass Off White | | | | |
| 3C | Bismuth(3) oxide[4] 5 g<br>1,3-Diphenyl-2-thiourea[4] 10 g | Gray | Gray | Gray | Gray | Pass Off White | Gray[1] | | | |
| 4C | Bismuth(3) oxide[4] 5 g<br>1,3-Diphenyl-2-thiourea[4] 10 g<br>Sodium carbonate[4] 3 g | Gray | Gray[3] | Gray | Very Light Brown | Pass Off White | | | | |

[1]Same after 6 minutes.
[3]Same after 5 minutes
[4]Commercially available from Aldrich Chemical Company, Inc., Milwaukee, WI.

EXAMPLE 13

Indicator inks were prepared as described above with the components in the amounts given in Table 13. The ink

TABLE 13

| Run No. | Components<br>a) Bismuth compound<br>b) Sulfur compound<br>c) Base or base generator | Response in Joslyn BIER Vessel (color after) | | | | Dry Heat | Response in AMSCO 3013-C Sterilizer (color after) | | | |
|---|---|---|---|---|---|---|---|---|---|---|
| | | 30 sec 134° C. | 2 min 134° C. | 3 min 121° C. | 10 min 121° C. | 30 min 141° C. | 0/1 min 132° C. | 3/1 min 132° C. | 3/1 min 121° C. | 10/1 min 121° C. |
| 1C | Bismuth subnitrate[4] 7 g<br>1,3-Di-o-tolyl-2-thiourea[4] 1.75 g | Light Brown | Brown | Beige | Brown | Fail Medium Brown | Brown | Medium Brown | | |
| 2C | Bismuth subnitrate[4] 7 g<br>1,3-Di-o-tolyl-2-thiourea[4] 1.75 g<br>Sodium carbonate[4] 0.5 g | Dark Brown | Very Dark Brown | Very Dark Brown | Very Dark Brown | Fail Medium Brown | Dark Brown | Dark Brown | | |
| 3C | Bismuth subcarbonate[2] 7 g<br>1,3-Di-o-tolyl-2-thiourea[4] 1.75 g | Cream | Dark Cream | Cream | Cream | Fail Dark Cream | Dark Cream | Beige | | |
| 4 | Bismuth subcarbonate[2] 7 g<br>1,3-Di-o-tolyl-2-thiourea[4] 1.75 g<br>Sodium carbonate[4] 0.5 g | Very Dark Brown | Black | Black | Black | Pass Yellow | Very Dark Brown | Black | | |
| 5C | Bismuth subnitrate[4] 7 g<br>1,3-Di-p-tolyl-2-thiourea[4] 1.75 g | Cream | Beige | White | Cream | Fail Medium Brown | Light Brown | Medium Brown | | |
| 6C | Bismuth subnitrate[4] 7 g<br>1,3-Di-p-tolyl-2-thiourea[4] 1.75 g<br>Sodium carbonate[4] 0.5 | Very Dark Brown | Black | Black | Black | Fail Medium Brown | Black | Black | | |
| 7 | Bismuth subcarbonate[2] 7 g<br>1,3-Di-p-tolyl-2-thiourea[4] 1.75 g | Cream | Beige | Beige | Dark Beige | Pass Dark Cream | Beige | Beige | | |
| 8 | Bismuth subcarbonate[2] 7 g<br>1,3-Di-p-tolyl-2-thiourea[4] 1.75 g<br>Sodium carbonate[4] 0.5 g | Black | Black | Black | Black | Pass Light Brown | Black | Black | | |

[2]Commercially available from J. T. Baker, Inc., Phillipsburg, NJ.
[4]Commercially available from Aldrich Chemical Company, Inc., Milwaukee, WI.

EXAMPLE 14

Indicator inks were prepared as described above with the components in the amounts given in Table 14. The ink suspension was coated, dried and tested as described above. The results of adding various bases to bismuth subcarbonate and 1-benzyl-3-methyl-2-thiourea are shown in Table 14.

Comparison Run 1C is similar to compositions described in Japanese Patent Kokai No. 4[1992]-364,174 (Takemura et al.). The sterilization conditions produced almost no reaction. The addition of sodium carbonate to the indicating ink composition in Run 2 caused the ink to turn brown in steam sterilization conditions. Lithium carbonate (Comparison Run 3C) had little effect on the color change in steam.

EXAMPLE 15

Indicator inks were prepared as described above with the components in the amounts given in Table 15. The ink suspension was coated, dried and tested as described above. The results of adding sodium carbonate to bismuth subcarbonate or bismuth subnitrate and 1-phenyl-2-thiourea are shown in Table 15.

Comparison Run 1C is similar to compositions described in Japanese Patent Kokai No. 4[1992]-364,174 (Takemura et al.). Not only did Run 1C not turn black in steam sterilization conditions, but it failed the dry heat test. The addition of sodium carbonate caused the indicating ink composition in Comparison Run 2C to turn black, but it failed the dry heat test. The ink composition in Comparison Run 3C rapidly turned black and also failed the dry heat test.

TABLE 14

| Run No. | Components<br>a) Bismuth compound<br>b) Sulfur compound<br>c) Base or base generator | Response in Joslyn BIER Vessel (color after) | | | | Dry Heat | Response in AMSCO 3013-C Sterilizer (color after) | | | |
|---|---|---|---|---|---|---|---|---|---|---|
| | | 30 sec 134° C. | 2 min 134° C. | 3 min 121° C. | 10 min 121° C. | 30 min 141° C. | 0/1 min 132° C. | 3/1 min 132° C. | 3/1 min 121° C. | 10/1 min 121° C. |
| 1C | Bismuth subcarbonate[2] 7 g<br>1-Benzyl-3-methylthiourea[4] 3.5 g | Light Yellow | Light Brown | Light Yellow | Light Brown | Pass | | | | |
| 2 | Bismuth subcarbonate[2] 7 g<br>1-Benzyl-3-methylthiourea[4] 3.5 g<br>Sodium carbonate[4] 0.5 g | White | Dark Dull Brown | Very Light Brown | Brown | Pass | | | | |
| 3C | Bismuth subcarbonate[2] 7 g<br>1-Benzyl-3-methylthiourea[4] 3.5 g<br>Lithium carbonate[5] 0.5 g | White | Light Brown | Pale Yellow | Light Brown | Pass | | | | |

[2]Commercially available from J. T. Baker, Inc., Phillipsburg, NJ.
[4]Commercially available from Aldrich Chemical Company, Inc., Milwaukee, WI.
[5]Commercially available from Fisher Chemical Company, Fair Lawn, NJ.

TABLE 15

| Run No. | Components<br>a) Bismuth compound<br>b) Sulfur compound<br>c) Base or base generator | Response in Joslyn BIER Vessel (color after) | | | | Dry Heat | Response in AMSCO 3013-C Sterilizer (color after) | | | |
|---|---|---|---|---|---|---|---|---|---|---|
| | | 30 sec 134° C. | 2 min 134° C. | 3 min 121° C. | 10 min 121° C. | 30 min 141° C. | 0/1 min 132° C. | 3/1 min 132° C. | 3/1 min 121° C. | 10/1 min 121° C. |
| 1C | Bismuth subcarbonate[2] 7 g<br>1-Phenyl-2-thiourea[4] 1.75 g | Light Brown | Medium Brown[1] | Light Brown | Slightly Darker Brown | Fail Medium Brown | Light Brown | Medium Brown[1] | | |
| 2C | Bismuth subcarbonate[2] 7 g<br>1-Phenyl-2-thiourea[4] 1.75 g<br>Sodium carbonate[4] 0.5 g | Very Dark Brown | Black | Black | Black | Fail Dark Brown | Black | Black | | |
| 3C | Bismuth subnitrate[4] 7 g<br>1-Phenyl-2-thiourea[4] 1.75 g | Black | Black | Black | Black | Fail Black | | | | |

[1]Same after 5 minutes.
[2]Commercially available from J. T. Baker, Inc., Phillipsburg, NJ.
[4]Commercially available from Aldrich Chemical Company, Inc., Milwaukee, WI.

EXAMPLE 16

Indicator inks were prepared as described above with the components in the amounts given in Table 16. The ink suspension was coated, dried and tested as described above. The results of adding sodium carbonate to bismuth subcarbonate and 1-allyl-2-hydroxyethyl-2-thiourea are shown in Table 16.

The ink composition in Comparison Run 1C turned brown in steam, but failed the dry heat test. The addition of a base to the ink composition (Comparison Run 2C) had no effect.

EXAMPLE 17

Indicator inks were prepared as described above with the components in the amounts given in Table 17. The ink suspension was coated, dried and tested as described above. The results of adding sodium carbonate to bismuth subcarbonate and 4,6-dihydroxy-2-mercaptopyrimidine are shown in Table 17.

Comparison Run 1C had almost no color change in steam. In Run 2, the addition of base turned the indicating ink composition brown.

TABLE 16

| Run No. | Components<br>a) Bismuth compound<br>b) Sulfur compound<br>c) Base or base generator | Response in Joslyn BIER Vessel (color after) | | | | Dry Heat | Response in AMSCO 3013-C Sterilizer (color after) | | | |
|---|---|---|---|---|---|---|---|---|---|---|
| | | 30 sec 134° C. | 2 min 134° C. | 3 min 121° C. | 10 min 121° C. | 30 min 141° C. | 0/1 min 132° C. | 3/1 min 132° C. | 3/1 min 121° C. | 10/1 min 121° C. |
| 1C | Bismuth subcarbonate[2] 7 g<br>1-allyl-2-hydroxyethylthiourea[4] 1.75 g | | Brown | | | Light Brown | Fail Black | | | |
| 2C | Bismuth subcarbonate[2] 7 g<br>1-allyl-2-hydroxyethylthiourea[4] 1.75 g<br>Sodium carbonate[4] 0.5 g | Brown | Dark Brown | | | Fail Black | | | | |

[2]Commercially available from J. T. Baker, Inc., Phillipsburg, NJ.
[4]Commercially available from Aldrich Chemical Company, Inc., Milwaukee, WI.

TABLE 17

| Run No. | Components<br>a) Bismuth compound<br>b) Sulfur compound<br>c) Base or base generator | Response in Joslyn BIER Vessel (color after) | | | | Dry Heat | Response in AMSCO 3013-C Sterilizer (color after) | | | |
|---|---|---|---|---|---|---|---|---|---|---|
| | | 30 sec 134° C. | 2 min 134° C. | 3 min 121° C. | 10 min 121° C. | 30 min 141° C. | 0/1 min 132° C. | 3/1 min 132° C. | 3/1 min 121° C. | 10/1 min 121° C. |
| 1C | Bismuth subcarbonate[2] 7 g<br>4,6-Dihydroxy-2-mercaptopyrimidine[4] 7 g | Light Orange | Buff | | | Cream | Light Orange | Pale Brown | | |

TABLE 17-continued

| | Components<br>a) Bismuth compound<br>Run b) Sulfur compound<br>No. c) Base or base generator | Response in<br>Joslyn BIER Vessel<br>(color after) | | | | Dry<br>Heat | Response in<br>AMSCO 3013-C Sterilizer<br>(color after) | | | |
|---|---|---|---|---|---|---|---|---|---|---|
| | | 30 sec<br>134° C. | 2 min<br>134° C. | 3 min<br>121° C. | 10 min<br>121° C. | 30 min<br>141° C. | 0/1 min<br>132° C. | 3/1 min<br>132° C. | 3/1 min<br>121° C. | 10/1 min<br>121° C. |
| 2 | Bismuth subcarbonate[2] 7 g<br>4,6-Dihydroxy-2-<br>mercaptopyrimidine[4] 7 g<br>Sodium carbonate[4] 1 g | Cream | Brown | | | Pass | Cream | Brown | | |

[2]Commercially available from J. T. Baker, Inc., Phillipsburg, NJ.
[4]Commercially available from Aldrich Chemical Company, Inc., Milwaukee, WI.

EXAMPLE 18

Indicator inks were prepared as described above with the components in the amounts given in Table 18. The ink suspension was coated, dried and tested as described above. The results of adding sodium carbonate to bismuth subcarbonate and 4-hydroxy-2-mercaptopyrimidine are shown in Table 18.

Comparison Run 1C had no color change in steam sterilization conditions. Apparently the sulfur compound did not generate any sulfur for the reaction and the addition of base in Run 2 had no effect on the color change.

EXAMPLE 19

Indicator inks were prepared as described above with the components in the amounts given in Table 19. The ink suspension was coated, dried and tested as described above. The results of adding sodium carbonate to bismuth subcarbonate and 3,4,5,6-tetrahydro-2-pyrimidinethiol are shown in Table 19.

Again Comparison Run 1C had no color change in steam sterilization conditions. Apparently the sulfur compound did not generate any sulfur for the color change and the addition of base in Run 2 had no effect.

TABLE 18

| | Components<br>a) Bismuth compound<br>Run b) Sulfur compound<br>No. c) Base or base generator | Response in<br>Joslyn BIER Vessel<br>(color after) | | | | Dry<br>Heat | Response in<br>AMSCO 3013-C Sterilizer<br>(color after) | | | |
|---|---|---|---|---|---|---|---|---|---|---|
| | | 30 sec<br>134° C. | 2 min<br>134° C. | 3 min<br>121° C. | 10 min<br>121° C. | 30 min<br>141° C. | 0/1 min<br>132° C. | 3/1 min<br>132° C. | 3/1 min<br>121° C. | 10/1 min<br>121° C. |
| 1C | Bismuth subcarbonate[2] 7 g<br>4-Hydroxy-2-<br>mercaptopyrimidine[4] 1.75 g | | White | | | White | | | | |
| 2C | Bismuth subcarbonate[2] 7 g<br>4-Hydroxy-2-<br>mercaptopyrimidine[4] 1.75 g<br>Sodium carbonate[4] 0.5 g | Pale<br>Yellow | Pale<br>Yellow | | | White | | | | |

[2]Commercially available from J. T. Baker Inc., Phillipsburg, NJ.
[4]Commercially available from Aldrich Chemical Company, Inc., Milwaukee, WI.

TABLE 19

| | Components<br>a) Bismuth compound<br>Run b) Sulfur compound<br>No. c) Base or base generator | Response in<br>Joslyn BIER Vessel<br>(color after) | | | | Dry<br>Heat | Response in<br>AMSCO 3013-C Sterilizer<br>(color after) | | | |
|---|---|---|---|---|---|---|---|---|---|---|
| | | 30 sec<br>134° C. | 2 min<br>134° C. | 3 min<br>121° C. | 10 min<br>121° C. | 30 min<br>141° C. | 0/1 min<br>132° C. | 3/1 min<br>132° C. | 3/1 min<br>121° C. | 10/1 min<br>121° C. |
| 1C | Bismuth subcarbonate[2] 7 g<br>3,4,5,6-Tetrahydro-2-<br>pyrimidinethiol[4] 1.75 g | | White | | | | White | | | |

TABLE 19-continued

| Run No. | Components<br>a) Bismuth compound<br>b) Sulfur compound<br>c) Base or base generator | Response in Joslyn BIER Vessel (color after) | | | | Dry Heat | Response in AMSCO 3013-C Sterilizer (color after) | | | |
|---|---|---|---|---|---|---|---|---|---|---|
| | | 30 sec 134° C. | 2 min 134° C. | 3 min 121° C. | 10 min 121° C. | 30 min 141° C. | 0/1 min 132° C. | 3/1 min 132° C. | 3/1 min 121° C. | 10/1 min 121° C. |
| 2C | Bismuth subcarbonate[2] 7 g<br>3,4,5,6-Tetrahydro-2-pyrimidinethiol[4] 1.75 g<br>Sodium carbonate[4] 0.5 g | White | White | | | White | | | | |

[2]Commercially available from J. T. Baker, Inc., Phillipsburg, NJ.
[4]Commercially available from Aldrich Chemical Company, Inc., Milwaukee, WI.

EXAMPLE 20

Indicator inks were prepared as described above with the components in the amounts given in Table 20. The ink suspension was coated, dried and tested as described above. The results of adding sodium carbonate to bismuth subcarbonate and 1-phenyl-3-thiosemicarbazide are shown in Table 20.

The ink composition in Comparison Run 1C turned brown in the AMSCO Sterilizer and the indicating ink composition in Run 2 turned dark brown with the addition of a base.

EXAMPLE 21

Indicator inks were prepared as described above with the components in the amounts given in Table 21. The ink suspension was coated, dried and tested as described above. The results of adding lithium carbonate to bismuth hydroxide and 1,3-diphenyl-2-thiourea are shown in Table 21.

The ink composition in Comparison Run 1C turned brown in steam sterilization conditions, but failed the dry heat test. The addition of a base in Comparison Run 2C increased the rate of color change, but still failed the dry heat test.

TABLE 20

| Run No. | Components<br>a) Bismuth compound<br>b) Sulfur compound<br>c) Base or base generator | Response in Joslyn BIER Vessel (color after) | | | | Dry Heat | Response in AMSCO 3013-C Sterilizer (color after) | | | |
|---|---|---|---|---|---|---|---|---|---|---|
| | | 30 sec 134° C. | 2 min 134° C. | 3 min 121° C. | 10 min 121° C. | 30 min 141° C. | 0/1 min 132° C. | 3/1 min 132° C. | 3/1 min 121° C. | 10/1 min 121° C. |
| 1C | Bismuth subcarbonate[2] 7 g<br>1-Phenyl-3-thiosemicarbazide[4] 7 g | | | | | Pass | Mottled Light Brown | Mottled Brown | | |
| 2 | Bismuth subcarbonate[2] 7 g<br>1-Phenyl-3-thiosemicarbazide[4] 7 g<br>Sodium carbonate[4] 2 g | Brown | Very Dark Brown | | | Pass | Very Dark Brown | Very Dark Brown | | |

[2]Commercially available from J. T. Baker, Inc., Phillipsburg, NJ.
[4]Commercially available from Aldrich Chemical Company, Inc., Milwaukee, WI.

TABLE 21

| Run No. | Components<br>a) Bismuth compound<br>b) Sulfur compound<br>c) Base or base generator | Response in Joslyn BIER Vessel (color after) | | | | Dry Heat | Response in AMSCO 3013-C Sterilizer (color after) | | | |
|---|---|---|---|---|---|---|---|---|---|---|
| | | 30 sec 134° C. | 2 min 134° C. | 3 min 121° C. | 10 min 121° C. | 30 min 141° C. | 0/1 min 132° C. | 3/1 min 132° C. | 3/1 min 121° C. | 10/1 min 121° C. |
| 1C | Bismuth hydroxide[4] 6 g<br>1,3-Diphenyl-2-thiourea[4] 1.75 g | Light Brown | Medium Brown | Light Brown | Brown | Fail Light Brown | Light Brown | Medium Brown | Light Brown | Brown |
| 2C | Bismuth hydroxide[4] 6 g<br>1,3-Diphenyl-2-thiourea[4] 1.75 g<br>Lithium Carbonate[5] 1.6 g | Very Dark Brown | Black | Very Dark Brown | Very Dark Brown | Fail Very Dark Brown | Very Dark Brown | Black | Very Dark Brown | Black |

[4]Commercially available from Aldrich Chemical Company, Inc., Milwaukee, WI.
[5]Commercially available from Fisher Chemical Company, Fair Lawn, NJ.

EXAMPLE 22

Indicator inks were prepared as described above with the components in the amounts given in Table 22. The ink suspension was coated, dried and tested as described above. The results of adding lithium carbonate to bismuth nitrate pentahydrate and 1,3-diphenyl-2-thiourea are shown in Table 22.

The ink composition in Comparison Run 1C did not turn dark enough in steam sterilization conditions. The addition of a base to the composition (Comparison Run 2C) caused the color change to black, but it failed the dry heat test.

EXAMPLE 24

Indicator inks were prepared as described above with the components in the amounts given in Table 24. The ink suspension was coated, dried and tested as described above. The results of adding sodium carbonate to bismuth subcarbonate and 2-thiohydantoin are shown in Table 24.

The ink composition in Comparison Run 1C changed color in steam sterilization conditions, but it was not sufficiently black or dark brown. In Run 2, the addition of base caused the ink composition color to change to red/brown before sterilization or exposure to dry heat. Sterilization conditions caused the red/brown to change to black and the composition remained red/brown in dry heat.

TABLE 22

| Run No. | Components<br>a) Bismuth compound<br>b) Sulfur compound<br>c) Base or base generator | Response in Joslyn BIER Vessel (color after) | | | | Dry Heat | Response in AMSCO 3013-C Sterilizer (color after) | | | |
|---|---|---|---|---|---|---|---|---|---|---|
| | | 30 sec 134° C. | 2 min 134° C. | 3 min 121° C. | 10 min 121° C. | 30 min 141° C. | 0/1 min 132° C. | 3/1 min 132° C. | 3/1 min 121° C. | 10/1 min 121° C. |
| 1C | Bismuth nitrate pentahydrate[4] 7 g<br>1,3-Diphenyl-2-thiourea[4] 1.75 g | Yellow | Yellow | Yellow | Yellow | Pass<br>Dark<br>Yellow | Yellow | Yellow | Yellow | Yellow |
| 2C | Bismuth nitrate pentahydrate[4] 7 g<br>1,3-Diphenyl-2-thiourea[4] 1.75 g<br>Lithium Carbonate[5] 1.6 g | Black | Black | Black | Black | Fail<br>Black | Black | Black | Black | Black |

[4]Commercially available from Aldrich Chemical Company, Inc., Milwaukee, WI.
[5]Commercially available from Fisher Chemical Company, Fair Lawn, NJ.

EXAMPLE 23

Indicator inks were prepared as described above with the components in the amounts given in Table 23. The ink suspension was coated, dried and tested as described above. The results of adding sodium carbonate to bismuth subcarbonate and 1,2-diethyl-2-thiobarbituric acid are shown in Table 23.

The ink composition in Comparison Run 1C did not change to a dark enough color in steam sterilization conditions. The addition of a base in Comparison Run 2C had no effect.

TABLE 23

| Run No. | Components<br>a) Bismuth compound<br>b) Sulfur compound<br>c) Base or base generator | Response in Joslyn BIER Vessel (color after) | | | | Dry Heat | Response in AMSCO 3013-C Sterilizer (color after) | | | |
|---|---|---|---|---|---|---|---|---|---|---|
| | | 30 sec 134° C. | 2 min 134° C. | 3 min 121° C. | 10 min 121° C. | 30 min 141° C. | 0/1 min 132° C. | 3/1 min 132° C. | 3/1 min 121° C. | 10/1 min 121° C. |
| 1C | Bismuth subcarbonate[2] 7 g<br>1,2-Diethyl-2-thiobarbituric acid[4] 7 g | Very Light Pink | Very Light Pink | | | | Very Light Pink | Very Light Pink | | |
| 2C | Bismuth subcarbonate[2] 7 g<br>1,2-Diethyl-2-thiobarbituric acid[4] 7 g<br>Sodium carbonate[4] 0.5 g | Cream | Pale Yellow | Cream | Cream | Pass<br>Cream | Cream | Cream | Cream | Cream |

[2]Commercially available from J. T. Baker, Inc., Phillipsburg, NJ.
[4]Commercially available from Aldrich Chemical Company, Inc., Milwaukee, WI.

TABLE 24

| | Components a) Bismuth compound b) Sulfur compound c) Base or base generator | Response in Joslyn BIER Vessel (color after) | | | | Dry Heat | Response in AMSCO 3013-C Sterilizer (color after) | | | |
|---|---|---|---|---|---|---|---|---|---|---|
| Run No. | | 30 sec 134° C. | 2 min 134° C. | 3 min 121° C. | 10 min 121° C. | 30 min 141° C. | 0/1 min 132° C. | 3/1 min 132° C. | 3/1 min 121° C. | 10/1 min 121° C. |
| 1C | Bismuth subcarbonate[2] 7 g 2-Thiohydantoin[4] 7 g | Mottled Light Tan | Mottled Dull Brown | Mottled Gray Brown | Dark Gray | Pass Cream | Mottled Light Brown | Mottled Dull Brown | | |
| 2 | Bismuth subcarbonate[2] 7 g 2-Thiohydantoin[4] 7 g Sodium Carbonate[4] 7 g | Black | Black | Black | Black | Pass[1] Red/ Brown | | Black | | |

[1]Initial color is red/brown and it stays that color.
[2]Commercially available from J. T. Baker, Inc., Phillipsburg, NJ.
[4]Commercially available from Aldrich Chemical Company, Inc., Milwaukee, WI.

EXAMPLE 25

Indicator inks were prepared as described above with the components in the amounts given in Table 25. The ink suspension was coated, dried and tested as described above. The results of adding sodium carbonate to bismuth subcarbonate and 2-mercaptobenzimidazole are shown in Table 25.

The ink composition of Comparison Run 1C had no color change in steam sterilization conditions. Apparently the sulfur compound did not generate any sulfur for the reaction and the addition of base in Comparison Run 2C had no effect on the reaction.

EXAMPLE 26

Indicator inks were prepared as described above with the components in the amounts given in Table 26. The ink suspension was coated, dried and tested as described above. The results of combining bismuth subcarbonate, bismuth oxychloride, bismuth oxide, bismuth subnitrate, or bismuth nitrate and thiourea are shown in Table 26.

The indicating ink compositions in Table 26 failed the dry heat test; therefore, base was not added to the compositions. Comparison Run 1C is similar to compositions described in Japanese Patent Kokai No. 4[1992]-364,174 (Takemura et al.) and to compositions described in Japanese Patent Kokai No. 4[1992]-62,746 (Koybayashi et al.).

TABLE 25

| | Components a) Bismuth compound b) Sulfur compound c) Base or base generator | Response in Joslyn BIER Vessel (color after) | | | | Dry Heat | Response in AMSCO 3013-C Sterilizer (color after) | | | |
|---|---|---|---|---|---|---|---|---|---|---|
| Run No. | | 30 sec 134° C. | 2 min 134° C. | 3 min 121° C. | 10 min 121° C. | 30 min 141° C. | 0/1 min 132° C. | 3/1 min 132° C. | 3/1 min 121° C. | 10/1 min 121° C. |
| 1C | Bismuth subcarbonate[2] 7 g 2-Mercaptobenzimidazole[4] 7 g | | | | | | White | White | | |
| 2C | Bismuth subcarbonate[2] 7 g 2-Mercaptobenzimidazole[4] 7 g Sodium carbonate[4] 0.5 g | | | | | | | White | | |

[2]Commercially available from J. T. Baker, Inc., Phillipsburg, NJ.
[4]Commercially available from Aldrich Chemical Company, Inc., Milwaukee, WI.

TABLE 26

| | Components a) Bismuth compound b) Sulfur compound c) Base or base generator | Response in Joslyn BIER Vessel (color after) | | | | Dry Heat | Response in AMSCO 3013-C Sterilizer (color after) | | | |
|---|---|---|---|---|---|---|---|---|---|---|
| Run No. | | 30 sec 134° C. | 2 min 134° C. | 3 min 121° C. | 10 min 121° C. | 30 min 141° C. | 0/1 min 132° C. | 3/1 min 132° C. | 3/1 min 121° C. | 10/1 min 121° C. |
| 1C | Bismuth subcarbonate[2] 7 g Thiourea[4] 7 g | Mottled Dark Brown | Very Dark Brown | | | Fail | Mottled Dark Brown | Very Dark Brown | | |
| 2C | Bismuth oxychloride[4] 7.5 g Thiourea[4] 7.5 g | | | | | Fail Black | Black | Black | | |

TABLE 26-continued

| | Components<br>a) Bismuth compound | Response in<br>Joslyn BIER Vessel<br>(color after) | | | | Dry<br>Heat | Response in<br>AMSCO 3013-C Sterilizer<br>(color after) | | | |
|---|---|---|---|---|---|---|---|---|---|---|
| Run<br>No. | b) Sulfur compound<br>c) Base or base generator | 30 sec<br>134° C. | 2 min<br>134° C. | 3 min<br>121° C. | 10 min<br>121° C. | 30 min<br>141° C. | 0/1 min<br>132° C. | 3/1 min<br>132° C. | 3/1 min<br>121° C. | 10/1 min<br>121° C. |
| 3C | Bismuth oxide[4] 7.5 g<br>Thiourea[4] 7.5 g | | | | | Fail Dark<br>Gray | Black | Black | | |
| 4C | Bismuth subnitrate[4] 7.5 g<br>Thiourea[4] 7.5 g | | | | | Fail<br>Black | Black | Black | | |
| 5C | Bismuth nitrate[4] 7.5 g<br>Thiourea[4] 7.5 g | | | | | Fail<br>Black | Black | Black | | |

[2]Commercially available from J. T. Baker, Inc., Phillipsburg, NJ.
[4]Commercially available from Aldrich Chemical Company, Inc., Milwaukee, WI.

EXAMPLE 27

Indicator inks were prepared as described above with the components in the amounts given in Table 27. The ink suspension was coated, dried and tested as described above. The results of combining bismuth oxychloride, bismuth oxide, bismuth subnitrate, bismuth nitrate, bismuth subcarbonate, and zinc oxide are shown in Table 27.

The ink compositions in Table 27 passed the dry heat test, but did not change color when exposed to steam sterilization conditions. Apparently zinc sulfide did not release sulfur under these conditions.

EXAMPLE 28

Indicator inks were prepared as described above with the components in the amounts given in Table 28. The ink suspension was coated, dried and tested as described above. The results of combining bismuth subcarbonate or bismuth oxychloride or bismuth oxide or bismuth subnitrate or bismuth nitrate and 4-phenyl-3-thiosemicarbazide or thiobenzanmide or thiosemicarbazide are shown in Table 28.

The indicating ink compositions in Table 28 failed the dry heat test; therefore, base was not added to the compositions.

TABLE 27

| | Components<br>a) Bismuth compound | Response in<br>Joslyn BIER Vessel<br>(color after) | | | | Dry<br>Heat | Response in<br>AMSCO 3013-C Sterilizer<br>(color after) | | | |
|---|---|---|---|---|---|---|---|---|---|---|
| Run<br>No. | b) Sulfur compound<br>c) Base or base generator | 30 sec<br>134° C. | 2 min<br>134° C. | 3 min<br>121° C. | 10 min<br>121° C. | 30 min<br>141° C. | 0/1 min<br>132° C. | 3/1 min<br>132° C. | 3/1 min<br>121° C. | 10/1 min<br>121° C. |
| 1C | Bismuth oxychloride[4] 7.5 g<br>Zinc sulfide 7.5 g | | | | | Pass<br>White | White | White | | |
| 2C | Bismuth oxide[4] 7.5 g<br>Zinc sulfide 7.5 g | | | | | Pass<br>Cream | Cream | Cream | | |
| 3C | Bismuth subnitrate[4] 7.5 g<br>Zinc sulfide 7.5 g | | | | | Pass<br>White | White | Very<br>Light<br>Gray | | |
| 4C | Bismuth nitrate[4] 7.5 g<br>Zinc sulfide 7.5 g | | | | | Pass<br>White | White | White | | |
| 5C | Bismuth subcarbonate[2] 7.5 g<br>Zinc sulfide 7.5 g | | | | | Pass<br>White | White | White | | |

[2]Commercially available from J. T. Baker, Inc., Phillipsburg, NJ.
[4]Commercially available from Aldrich Chemical Company, Inc., Milwaukee, WI.

TABLE 28

| | Components<br>a) Bismuth compound | Response in<br>Joslyn BIER Vessel<br>(color after) | | | | Dry<br>Heat | Response in<br>AMSCO 3013-C Sterilizer<br>(color after) | | | |
|---|---|---|---|---|---|---|---|---|---|---|
| Run<br>No. | b) Sulfur compound<br>c) Base or base generator | 30 sec<br>134° C. | 2 min<br>134° C. | 3 min<br>121° C. | 10 min<br>121° C. | 30 min<br>141° C. | 0/1 min<br>132° C. | 3/1 min<br>132° C. | 3/1 min<br>121° C. | 10/1 min<br>121° C. |
| 1C | Bismuth subcarbonate[2] 7 g<br>4-Phenyl-3-<br>thiosemicarbazide[4] 7 g | | | | | Fail | Black | Black | | |

TABLE 28-continued

| | Components<br>a) Bismuth compound | Response in<br>Joslyn BIER Vessel<br>(color after) | | | | Dry<br>Heat | Response in<br>AMSCO 3013-C Sterilizer<br>(color after) | | | |
|---|---|---|---|---|---|---|---|---|---|---|
| Run<br>No. | b) Sulfur compound<br>c) Base or base generator | 30 sec<br>134° C. | 2 min<br>134° C. | 3 min<br>121° C. | 10 min<br>121° C. | 30 min<br>141° C. | 0/1 min<br>132° C. | 3/1 min<br>132° C. | 3/1 min<br>121° C. | 10/1 min<br>121° C. |
| 2C | Bismuth subcarbonate[2] 7 g<br>4-Phenyl-3-<br>thiosemicarbazide[4] 3.5 g | | | | | Fail | Very<br>Dark<br>Brown | Very<br>Dark<br>Brown | | |
| 3C | Bismuth subcarbonate[2] 7 g<br>Thiobenzamide[4] 7 g | Dull<br>Dark<br>Brown | Dull<br>Black | | | Fail | Dull<br>Dark<br>Brown | Dull<br>Black | | |
| 4C | Bismuth subcarbonate[2] 7 g<br>Thiosemicarbazide[4] 7 g | Black | Black | | | Fail | Black | Black | | |
| 5C | Bismuth oxychloride[4] 7.5 g<br>Thiosemicarbazide[4] 7.5 g | | | | | Fail Black | Black | Black | | |
| 6C | Bismuth oxide[4] 7.5 g<br>Thiosemicarbazide[4] 7.5 g | | | | | Fail Black | Black | Black | | |
| 7C | Bismuth subnitrate[4] 7.5 g<br>Thiosemicarbazide[4] 7.5 g | | | | | Fail Black | Black | Black | | |
| 8C | Bismuth nitrate[4] 7.5 g<br>Thiosemicarbazide[4] 7.5 g | | | | | Fail Black | Black | Black | | |

[2]Commercially available from J. T. Baker, Inc., Phillipsburg, NJ.
[4]Commercially available from Aldrich Chemical Company, Inc., Milwaukee, WI.

EXAMPLE 29 selected samples from the examples that turned black, very dark brown, dark brown and beige as well as an unexposed sample of the indicating ink composition coated on the paper substrate described above were evaluated for the color coordinates. The color coordinates for standard daylight conditions were measured for each sample using a "DIANO MATCH-SCAN II" spectrophotometer (Bausch and Lomb Inc.) with a 8 mm diameter sample port. The L*, a*, and b* reflection color coordinates were obtained using the standard white color tile in the reflection sample port. The results are reported in Table 29.

TABLE 29

| Run Number | Observed Color | L* | a* | b* |
|---|---|---|---|---|
| Control | Off White | 97.68 | −1.87 | 10.31 |
| 1 | Black | 30.62 | 0.49 | 1.26 |
| 2 | Black | 29.92 | 0.97 | 3.22 |
| 3 | Black | 30.52 | 1.12 | 2.67 |
| 4 | Black | 27.09 | 0.95 | 2.55 |
| 5 | Black | 32.85 | 0.56 | 1.94 |
| 6 | Very Dark Brown | 34.75 | 1.33 | 4.35 |
| 7 | Very Dark Brown | 38.04 | 1.80 | 4.70 |
| 8 | Dark Brown | 40.98 | 2.79 | 7.87 |
| 9 | Dark Brown | 42.29 | 2.66 | 7.76 |
| 10 | Brown | 53.06 | 6.30 | 17.20 |
| 11 | Brown | 57.07 | 7.42 | 19.72 |
| 12 | Beige | 76.78 | 8.34 | 34.59 |

The complete disclosure of all patents, patent documents, and publications cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A steam sterilization indicator composition comprising:
  (a) a bismuth compound;
  (b) a sulfur source selected from the group consisting of elemental sulfur and an organic sulfur compound; and
  (c) a compound capable of generating alkaline conditions when exposed to steam; wherein when exposed to steam, after about 2 minutes at 134° C., after about 3 minutes at 132° C., or after about 10 minutes at 121° C., the composition noticeably changes color; and when exposed to dry heat, at a temperature of about 141° C. for about 30 minutes, either does not change color or changes color to one that is markedly different from the color formed when the same composition is exposed to steam.

2. The composition of claim 1 wherein the sulfur source is an organic sulfur compound.

3. The composition of claim 1 wherein the compound capable of generating alkaline conditions when exposed to steam is a basic compound or is capable of generating a basic compound when exposed to steam.

4. The composition of claim 1 which upon exposure to steam changes to a color having an L* value of less than about 50.

5. A steam sterilization indicator composition comprising:
  (a) a bismuth compound;
  (b) a sulfur source selected from the group consisting of elemental sulfur, 1-(2-methoxyphenyl)-2-thiourea, 1-allyl-2-thiourea, 1-methyl-2-thiourea, 1-ethyl-2-thiourea, 1,3-dimethyl-2-thiourea, 1-phenyl-3-thiosemicarbazide, 1,3-diphenyl-2-thiourea, 1-benzyl-3-methyl-2-thiourea, 1,3-di-o-tolyl-2-thiourea, 1,3-di-p-tolyl-2-thiourea, 4,6-dihydroxy-2-mercaptopyrimidine, and 2-thiohydantoin; and
  (c) a compound capable of generating alkaline conditions when exposed to steam;
  wherein when exposed to steam, after about 2 minutes at 134° C., after about 3 minutes at 132° C., or after about 10 minutes at 121° C., the composition noticeably changes color; and when exposed to dry heat, at a temperature of about 141° C. for about 30 minutes, either does not change color or changes color to one that is markedly different from the color formed when the same composition is exposed to steam.

6. The composition of claim 1 wherein the bismuth compound is selected from the group consisting of bismuth oxychloride and bismuth subcarbonate.

7. The composition of claim 1 wherein the compound capable of generating alkaline conditions when exposed to steam is selected from the group consisting of sodium carbonate, sodium bicarbonate, lithium carbonate, barium hydroxide, calcium hydroxide, sodium acetate, potassium salt of 2,4-dihydroxybenzoic acid, lithium salt of 2,4-dihydroxybenzoic acid, potassium salt of 2,4,6-trihydroxybenzoic acid, and lithium salt of 2,4,6- trihydroxybenzoic acid.

8. The composition of claim 1 further comprising a binder.

9. The composition of claim 8 wherein the binder comprises a methyl/n-butylmethacrylate copolymer.

10. The composition of claim 9 further comprising surfactants, defoamers, fillers, pigments, plasticizers, flow aids, or solvents.

11. The composition of claim 1 which is coated on a substrate.

12. The composition of claim 11 wherein the substrate is a tape.

13. The composition of claim 11 wherein the substrate is selected from the group consisting of paper, coated paper, cardboard, plastics, metallised material, metal foil, non-woven material, and woven textile materials.

14. The composition of claim 13 wherein the paper is saturated with a rubber/resin solution or a natural or synthetic latex.

15. A steam sterilization indicator composition comprising:
  (a) a bismuth compound selected from the group consisting of bismuth oxychloride and bismuth subcarbonate;
  (b) a sulfur source selected from the group consisting of elemental sulfur, 1-(2-methoxyphenyl)-2-thiourea, 1-allyl-2-thiourea, 1-methyl-2-thiourea, 1-ethyl-2-thiourea, 1,3-dimethyl-2-thiourea, 1-phenyl-3-thiosemicarbazide, 1,3-diphenyl-2-thiourea, 1-benzyl-3-methyl-2-thiourea, 1,3-di-o-tolyl-2-thiourea, 1,3-di-p-tolyl-2-thiourea, 4,6-dihydroxy-2-mercaptopyrimidine, and 2-thiohydantoin; and
  (c) a compound capable of generating alkaline conditions when exposed to steam, which is selected from the group consisting of sodium carbonate, sodium bicarbonate, lithium carbonate, barium hydroxide, calcium hydroxide, sodium acetate, potassium salt of 2,4-dihydroxybenzoic acid, lithium salt of 2,4-dihydroxybenzoic acid, potassium salt of 2,4,6-trihydroxybenzoic acid, and lithium salt of 2,4,6- trihydroxybenzoic acid.

16. The composition of claim 15 wherein when exposed to steam the composition noticeably changes color and when exposed to dry heat either does not change color or changes color to one that is markedly different from the color formed when the same composition is exposed to steam.

17. A steam sterilization indicator composition preparable by combining components comprising:
  (a) a bismuth compound;
  (b) a sulfur source selected from the group consisting of elemental sulfur and an organic sulfur compound; and
  (c) a compound capable of generating alkaline conditions when exposed to steam; wherein when exposed to steam, after about 2 minutes at 134° C., after about 3 minutes at 132° C., or after about 10 minutes at 121° C., the composition noticeably changes color; and when exposed to dry heat, at a temperature of about 141° C. for about 30 minutes, either does not change color or changes color to one that is markedly different from the color formed when the same composition is exposed to steam.

18. A steam sterilization indicator composition preparable by combining components comprising:
  (a) a bismuth compound selected from the group consisting of bismuth oxychloride and bismuth subcarbonate;
  (b) a sulfur source selected from the group consisting of elemental sulfur, 1-(2-methoxyphenyl)-2-thiourea, 1-allyl-2-thiourea, 1-methyl-2-thiourea, 1-ethyl-2-thiourea, ,1,3-dimethyl-2-thiourea, 1-phenyl-3-thiosemicarbazide, 1,3-diphenyl-2-thiourea, 1-benzyl-3-methyl-2-thiourea, 1,3-di-o-tolyl-2-thiourea, 1,3-di-p-tolyl-2-thiourea, 4,6-dihydroxy-2-mercaptopyrimidine, and 2-thiohydantoin; and
  (c) a compound capable of generating alkaline conditions when exposed to steam, which is selected from the group consisting of sodium carbonate, sodium bicarbonate, lithium carbonate, barium hydroxide and calcium hydroxide or a base generator e.g. sodium acetate, potassium salt of 2,4-dihydroxybenzoic acid, lithium salt of 2,4-dihydroxybenzoic acid, potassium salt of 2,4,6-trihydroxybenzoic acid, and lithium salt of 2,4,6- trihydroxybenzoic acid.

19. A steam sterilization indicator comprising a substrate having coated on at least a portion of one major surface thereof a steam sterilization indicator composition comprising:
  (a) a bismuth compound;
  (b) a sulfur source selected from the group consisting of elemental sulfur and an organic sulfur compound; and
  (c) a compound capable of generating alkaline conditions when exposed to steam; wherein when exposed to steam, after about 2 minutes at 134° C., after about 3 minutes at 132° C., or after about 10 minutes at 121° C., the composition noticeably changes color; and when exposed to dry heat, at a temperature of about 141° C. for about 30 minutes, either does not change color or changes color to one that is markedly different from the color formed when the same composition is exposed to steam.

20. A steam sterilization indicator comprising a substrate having coated on at least a portion of one major surface thereof a steam sterilization indicator composition comprising:
  (a) a bismuth compound selected from the group consisting of bismuth oxychloride and bismuth subcarbonate;
  (b) a sulfur source selected from the group consisting of elemental sulfur, 1-(2-methoxyphenyl)-2-thiourea, 1-allyl-2-thiourea, 1-methyl-2-thiourea, 1-ethyl-2-thiourea, 1,3-dimethyl-2-thiourea, 1-phenyl-3-thiosemicarbazide, 1,3-diphenyl-2-thiourea, 1-benzyl-3-methyl-2-thiourea, 1,3-di-o-tolyl-2-thiourea, 1,3-di-p-tolyl-2-thiourea, 4,6-dihydroxy-2-mercaptopyrimidine, and 2-thiohydantoin; and
  (c) a compound capable of generating alkaline conditions when exposed to steam, which is selected from the group consisting of sodium carbonate, sodium bicarbonate, lithium carbonate, barium hydroxide, calcium hydroxide, sodium acetate, potassium salt of 2,4-dihydroxybenzoic acid, lithium salt of 2,4-dihydroxybenzoic acid, potassium salt of 2,4,6-trihydroxybenzoic acid, and lithium salt of 2,4,6-trihydroxybenzoic acid.

21. The composition of claim 1 which is lead-free.
22. The composition of claim 15 which is lead-free.
23. The composition of claim 17 which is lead-free.
24. The composition of claim 18 which is lead-free.
25. The indicator of claim 19 wherein the composition is lead-free.

26. The indicator of claim 20 wherein the composition is lead-free.

27. A steam sterilization indicator comprising a substrate having coated on at least a portion of one major surface thereof a steam sterilization indicator composition preparable by combining components comprising:
   (a) a bismuth compound;
   (b) a sulfur source selected from the group consisting of elemental sulfur and an organic sulfur compound; and
   (c) a compound capable of generating alkaline conditions when exposed to steam; wherein when exposed to steam, after about 2 minutes at 134° C., after about 3 minutes at 132° C., or after about 10 minutes at 121° C., the composition noticeably changes color; and when exposed to dry heat, at a temperature of about 141° C. for about 30 minutes, either does not change color or changes color to one that is markedly different from the color formed when the same composition is exposed to steam.

28. The indicator of claim 27 wherein the composition is lead-free.

29. A steam sterilization indicator comprising a substrate having coated on at least a portion of one major surface thereof a steam sterilization indicator composition preparable by combining components comprising:
   (a) a bismuth compound selected from the group consisting of bismuth oxychloride and bismuth subcarbonate;
   (b) a sulfur source selected from the group consisting of elemental sulfur, 1-(2-methoxyphenyl)-2-thiourea, 1-allyl-2-thiourea, 1-methyl-2-thiourea, 1-ethyl-2-thiourea, 1,3-dimethyl-2-thiourea, 1-phenyl-3-thiosemicarbazide, 1,3-diphenyl-2-thiourea, 1-benzyl-3-methyl-2-thiourea, 1,3-di--tolyl-2-thiourea, 1,3-di--tolyl-2-thiourea, 4,6-dihydroxy-2-mercaptopyrimidine, and 2-thiohydantoin; and
   (c) a compound capable of generating alkaline conditions when exposed to steam, which is selected from the group consisting of sodium carbonate, sodium bicarbonate, lithium carbonate, barium hydroxide, calcium hydroxide, sodium acetate, potassium salt of 2,4-dihydroxybenzoic acid, lithium salt of 2,4-dihydroxybenzoic acid, potassium salt of 2,4,6-trihydroxybenzoic acid, and lithium salt of 2,4,6-trihydroxybenzoic acid.

30. The indicator of claim 29 wherein the composition is lead-free.

31. The composition of claim 1 wherein the bismuth compound is not the sulfur source.

32. The composition of claim 2 wherein the bismuth compound is selected from the group consisting of bismuth oxychloride and bismuth subcarbonate.

33. The composition of claim 32 which is lead-free.

34. The composition of claim 17 wherein the bismuth compound is not the sulfur source.

35. The composition of claim 19 wherein the bismuth compound is not the sulfur source.

36. The indicator of claim 27 wherein the bismuth compound is not the sulfur source.

* * * * *